(12) United States Patent
Rieutord et al.

(10) Patent No.: US 7,688,946 B2
(45) Date of Patent: Mar. 30, 2010

(54) METHOD AND DEVICE FOR MEASURING BOND ENERGY

(75) Inventors: Francois Rieutord, Saint Egreve (FR); Hubert Moriceau, Saint Egreve (FR); Benoit Bataillou, Ghent (BE)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 11/666,368

(22) PCT Filed: Oct. 24, 2005

(86) PCT No.: PCT/FR2005/050891

§ 371 (c)(1),
(2), (4) Date: Apr. 25, 2007

(87) PCT Pub. No.: WO2006/045979

PCT Pub. Date: May 4, 2006

(65) Prior Publication Data

US 2008/0063143 A1 Mar. 13, 2008

(30) Foreign Application Priority Data

Oct. 26, 2004 (FR) .................................. 04 52442

(51) Int. Cl.
*G01N 23/20* (2006.01)
(52) U.S. Cl. .......................................... 378/82; 378/70
(58) Field of Classification Search ................... 378/70, 378/82–90
See application file for complete search history.

(56) References Cited

U.S. PATENT DOCUMENTS 5,007,071 A * 4/1991 Nakano et al. ................ 378/74

2003/0128809 A1 * 7/2003 Umezawa et al. ............. 378/70

OTHER PUBLICATIONS

International Search Report, PCT/FR2005/050891, 4 pgs., (Oct. 3, 2006).
Schnell, Ralf et al., "Direct Correlation Between Interfacial Width And Adhesion In Glassy Polymers" Macromolecules; Macromolecules Apr. 7, 1998 ACS, Washington, DC, USA, vol. 31, No. 7, (Apr. 7, 1998), pp. 2284-2292, XP002331093.
Pellegrini, N.N. et al., "Random Copolymer/homopolymer Interfacial Widths As A Function Of Copolymer Composition", Polymer, Elsevier Science Publishers B.V., GB, vol. 41, No. 7, (Mar. 2000), pp. 2701-2704, XP004244271, ISSN: 0032-3861.
Moriceau, H. et al., "Interest Of A Short Plasma Treatment To Achieve SI-SIO$_2$-SI Bonded Structures", Electrochem. Soc. Proc.; Electrochemical Society Proceedings; Semiconductor Wafer Bonding VII: Science, Technology, and Applications Proceedings of the International Symposium 2003, vol. 19, 2003, pp. 110-117, XP009048675.

(Continued)

*Primary Examiner*—Hoon Song
(74) *Attorney, Agent, or Firm*—Nixon Peabody LLP

(57) ABSTRACT

The adhesion between two layers, in particular two thin layers of a microelectronic device, is a data item of importance. It was found that the closure ratio of the interface could be used, in non-destructive manner, to determine a measurement of bond energy. A method and a device using a magnitude characteristic of this length are described, in particular using low incidence X-ray reflection and electronic density at the interface.

18 Claims, 1 Drawing Sheet

OTHER PUBLICATIONS

Rieutord, F. et al., "High-Energy X-Ray Reflectivity Of Buried Interfaces Created By Wafer Bonding", Physical Review, B. Condensed Matter, American Institute of Physics, New York, US, vol. 63, No. 12, (Mar. 15, 2001), pp. 125408-1-125408-5, XP001147457, ISSN: 0163-1829.

Tomasella, E. et al., "Structural And Mechanical Properties Of a-C:H Thin Films Grown By RF-PECVD", Diamond and Related Materials, Elsevier Science Publishers, Amsterdam, NL, vol. 13, No. 9, (Sep. 2004), pp. 1618-1624, Xpoo4518692, ISSN: 0925-9635.

Kim, Jangsoon et al., "Graxing Incidence X-Ray Diffraction Studies On The Structures Of Polyurethane Films And Their Effects On Adhesion To A1 Substrates", Polymer, Elservier Science Publishers B. V., GB, vol. 44, No. 21, (Oct. 2003), pp. 6663-6674, XP004456167, ISSN: 0032-3861.

Weichel, S. et al., "Fusion Bonding Of Si Wafers Investigated by X Ray Diffraction", Applied Physics Letters, American Institute of Physics. New York, US, vol. 76, No. 1, (Jan. 3, 2000), pp. 70-72, XP012024746; ISSN: 0003-6951.

Moshe Deutsch, Benjamin M. Ocko, "X-Ray And Neutron Reflectivity", Encyclopedia of Applied Physics, vol. 23, 1998, pp. 479-490, XP002331094 Weinheim, ISBN: 3-527-29476-7.

Poulsen, M. et al., "Towards A Microscopic Understanding Of Plasma Activated Bonding", Electrochem. Soc. Proc.; Electrochemical Society Proceedings; Semiconductor Wafer Bonding VII: Science, Technology, and Applications Proceeding of the International Symposium 2003, vol. 19, 2003, pp. 248-258, XP009048642.

Maszara, W.P. et al., "Bonding Of Silicon Wafers For Silicon-On-Insulator", J. Appl Phys. (1988); 64: pp. 4943-4950, (Document Cited in the Specification).

Bataillou, B., et al., "Direct Inversion Of Interfacial Reflectivity Data Using The Patterson Function", J. Appl Cryst (2003); 36: pp. 1352-1355 (Document Cited in the Specification).

Johnson, K.L., "Contact Mechanics", (1985), Chapter 13 (Rought Surfaces), pp. 397-416, Cambridge University Press.

Born, Max et al., "Principles Of Optics" *Electromagnetic Theory of Propagation, Interference and Diffraction of Light*, 6$^{th}$ Edition, (1980), Pergamon Press.

* cited by examiner

METHOD AND DEVICE FOR MEASURING BOND ENERGY

CROSS REFERENCE TO RELATED APPLICATIONS OR PRIORITY CLAIM

This application is a national phase of International Application No. PCT/FR2005/050891 entitled "Method And Device For Measuring Adhesion Energy", which was filed on Oct. 24, 2005, which was not published in English, and which claims priority of the French Patent Application No. 04 52442 filed Oct. 26, 2004.

TECHNICAL AREA AND PRIOR ART the invention relate to edherence between two surfaces. More particularly, the invention concerns a method and device enabling measurement of bond energy at the interface, and its application to layers assembled by molecular bonding.

Measuring the adhesion of a thin layer on a substrate is a problem which arises in a large number of technological processes, and in particular in microelectronics. In general, the estimation of this adhesion is accompanied by destruction of the sample: the methods used to measure bond energy are generally based on crack-forming mechanical resistance tests.

In particular, adhesion is an important criterion for molecular bonding, a generic technique used to assemble different materials without having recourse to any outside adhesive. This technique has numerous applications, e.g. the fabrication of Silicon-On-Insulator (SOI) substrates in which two silicon wafers are assembled, at least one thereof being surface oxidized i.e. coated with an insulating oxide layer. One of the wafers may then be thinned, e.g. by fracture after implantation, mechanical-chemical attack, etc. The SOI wafer thus obtained therefore consists of a layer bonded onto a mechanical support.

SOI wafers generally have to undergo different successive treatments, e.g. annealing, depositing, mechanical stresses; in some cases the layer is detached from the support for transfer onto another substrate to form more complex stacks. It is therefore important, for the fabrication and use of these products, to be able to control and quantify the bond energy at different stages of the process.

At the present time, the chief method used for measuring adhesion energy, in the case of molecular bonding, is the so-called "blade" method: a calibrated spacer device is inserted between the two bonded wafers and the induced detachment is measured: this detachment is greater the weaker the bonding energy (Maszara W P et al <<Bonding of silicon wafers for silicon-on-insulators>>; *J Appl Phys* 1988; 64:4943-4950). However, this method only applies to rigid wafers, and is therefore not suitable for evaluating the energy of a layer thinned on a substrate. Additionally, the insertion of the spacer device is considered destructive since major mechanical action is applied to the surface of the SOI assembly which must be partially forced apart.

DESCRIPTION OF THE INVENTION

The invention sets out to overcome the mentioned shortcomings and to measure bond energy in non-destructive manner.

In particular, the invention concerns the measurement of bond energy using determination of the closure ratio of the interface, or of a magnitude characteristic thereof, e.g. the deficit of electronic density at the interface. The closure ratio here is measured on the scale of atom bonds, i.e. at nanometric level: its determination is therefore not related to counting macroscopic defects, such as <<bubbles>>, at the interface. The invention is adapted in particular for measuring the adhesion initiated by molecular bonding, in particular on microelectronic substrates.

According to one of its aspects, the invention relates to a method for measuring the bond energy between two surfaces comprising the determination of electronic density deficit at the interface. Advantageously, determination of the electronic intensity deficit is performed using low incidence X-ray reflection on the interface. According to another aspect, the density deficit of neutron diffusion length is used.

Preferably, bond energy derives from electronic density deficit, from diffusion wavelength deficit, or from closure ratio, using a calibration.

The invention also concerns a device which can be used to implement the method of the invention. In particular, the device of the invention comprises means to measure closure ratio (at nanometer scale) or one of its characteristic magnitudes, such as electronic density deficit or diffusion wavelength deficit. Advantageously, the measurement means include means for extracting this information from a graph representing the coefficient of X-ray reflection by the interface according to angle of incidence, which is preferably small. The device may comprise means for x-ray detection and for storage of the detected reflection coefficient, in relation to a variable angle of incidence. Neutrons may be used instead of X-rays.

According to one preferred embodiment, the device of the invention comprises a calibration profile to calibrate bond energy in relation to closure ratio, to electronic density deficit or to diffusion wavelength deficit, and means for comparing the closure ratio or determined density deficit with this profile.

BRIEF DESCRIPTION OF THE DRAWINGS

The characteristics and advantages of the invention will be better understood on reading the following description with reference to the appended drawings, given for illustrative purposes and in no way limiting.

DETAILED DESCRIPTION OF PARTICULAR EMBODIMENTS

Figure 1:
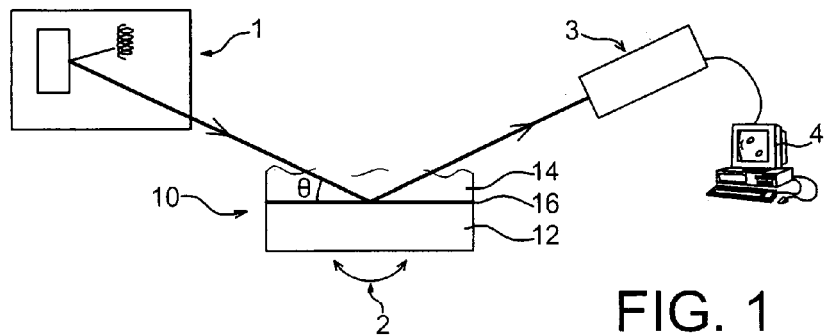
FIG. 1 shows a set-up for implementing a measurement method according to a preferred embodiment of the invention.

When studying the mechanisms of bonding, the applicant found that bond energy is related to the structure of the interface, i.e. to the distribution of matter. In particular, the interfacial closure ratio, defined as the ratio of the surface of a compound actually in contact, at nanometric scale, with a substrate to the total surface area of this contact, can be related to the bond energy between the support and the compound, which means that measurement via this intermediary is possible. The invention follows from these observations.

Generally, an adhering interface is formed of an alternation of bonded areas and non-bonded areas. In particular, with thin films assembled by molecular bonding, the distance between the layers at the non-bonded areas of the interface may be extremely small, typically in the order of a nanometer. Evidencing the surface which is not in contact therefore requires a very sensitive technique.

To measure the closure ratio or a magnitude characteristic thereof, using a non-destructive technique, it was found that X-rays are particularly suitable on account of their short wavelength in particular, typically in the order 0.1 nm.

Yet, it has already been shown that the measurement of the coefficient of X-ray reflection on the interface according to angle of incidence, makes it possible using appropriate processing i.e. an Inverse Fourier Transformation or a matrix method of multilayer optics (described for example in the work by Born M and Wolf E: *Principle of Optics,* 6th Edition, 1980, Pergamon Press), to determine the profile of electronic density via the interface i.e. by the number of electrons per unit volume measured at the interface (see for example Bataillou B, Moriceau H, Rieutord F: <<Direct inversion of interfacial reflectivity data using the Patterson function>>; *J Appl Cryst* 2003; 36:1352-1355).

Yet if the closure ratio is 100% i.e. if there are no contactless areas, the electronic density $\rho$ is identical to that of the bonded materials, in particular to that of silicon denoted $\rho_{Si}$ for SOI wafers of silicon on silicon type. In parallel, if only a fraction is bonded, the electronic density $\rho$ at the interface is only a fraction of the electronic density $\rho_{Si}$ of solid silicon: in fact the electronic density profile obtained generally has the form of an electronic density deficit $\Delta\rho$ at the bond interface, a deficit that is lesser the more adhesion is strong (FIG. 2B).

The closure ratio can therefore be deduced from the electronic density deficit $\Delta\rho$ in accordance with a function which can be calibrated in a few points. It is also possible to use adhesion models between rough surfaces to obtain the desired correlation. A description of some of these models can be found for example in Johnson K L: *Contact Mechanics,* 1985, Cambridge University Press.

The correspondence between electronic density deficit and bond energy can also be deduced from a master curve, or sampling profile.

Apparatus which can be used to implement the measurement method of the invention also advantageously comprises an X-ray source 1, a goniometer 2 and a detector 3 such as illustrated FIG. 1. A device 4 is connected to the detector 3, e.g. a microcomputer to store the detected information. Advantageously, the device 4 is coupled to programming means implementing the calculations or comparisons according to the invention to obtain results of bond energy E.

A compound 10, e.g. a SOI wafer comprising a Si layer 12 and a thin Si layer 14, is positioned on the goniometer 2. One of the advantages of the method of the invention is that it is non-destructive, and does not require any special preparation of the compound 10.

The interface 16 between the substrate 12 and the surface layer 14 is subjected to X-ray radiation emitted by source 1; the intensity reflected by the interface 16 is measured by the detector 3 and normalized by device 4 according to the intensity of the direct incident beam measured during the experiment, in order to obtain the reflection coefficient R of the interface 16 for X-rays. By means of the goniometer 2, the angle of incidence $\theta$ may vary, and the coefficient of reflection is measured in relation to the angle of incidence $\theta$ of the rays emitted by the source 1; generally, fairly small angles of incidence, from a fraction of a degree to a few degrees, are scanned.

Figure 2A:
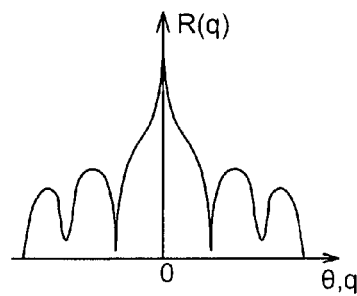
FIG. 2 schematically illustrates the steps of the measurement method according to one embodiment of the invention.
Figure 2B:
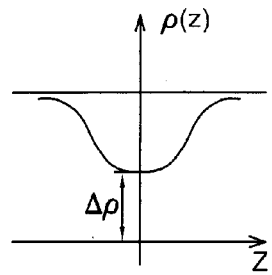

Mostly, the coefficient of reflection R decreases with the angle of incidence $\theta$, and is often represented in relation to the vertical component q of the transferred wave vector ($q=4\pi/\lambda \sin\theta$, where $\lambda$ wavelength of the radiation used): see FIG. 2A.

From the coefficient curve R in relation to q, it is possible, as mentioned above, to determine the profile of electronic density $\rho(z)$ about the interface, and the electronic density $\Delta\rho$ at the interface 16: FIG. 2B.

Figure 2C:
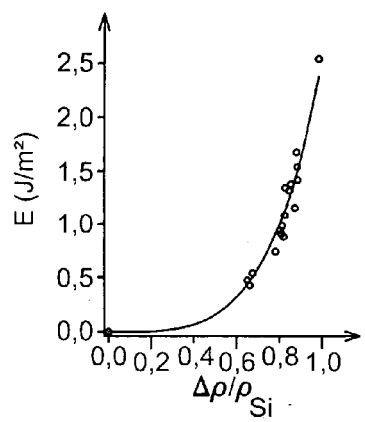

Since electronic density $\rho$ is related to the bonded fraction of the interface, a simple function is used to calculate bond energy E from the electronic density $\Delta\rho$ at the interface 16 between two layers 12, 14 of densities $\rho_{Si}$. This function may be calculated from adhesion models between rough surfaces or simply calibrated from a few points where energy is measured using the so-called <<blade>> method. Therefore, in FIG. 2C, the points shown on the curve correspond to series of measurements, using the Maszara technique (bonding of thick wafers) described in the above-mentioned reference, to measure bond energy on silicon/silicon or silicon/oxide interfaces.

The different steps can be performed using the same microcomputer 4, or a detection device may include separate means to obtain and store each intermediate result.

The method of the invention has been validated on hydrophobic and hydrophilic bonds at different annealing temperatures and which have undergone different surface treatments intended to modify the bond energy. Results have shown that the method gives reliable results.

Having regard to the extend of radiation absorption by the layers, it is preferable that the thickness of the upper layer 14 of the compound 10 should be one micron or less, using conventional sources (e.g. copper anode for the X-ray tube) and in materials such as silicon. This limit may be increased when using less absorbed radiation for example, such as hard X-rays or neutrons, or less absorbent materials. In particular, for neutron radiation, the intimate contact ratio is advantageously determined by evaluation of the density deficit of diffusion length, which is a magnitude that is characteristic of the neutron/core interaction.

The invention claimed is:

1. A non-destructive measurement device for measuring an adhesion energy at an interface between two layers, comprising:

means for measuring a reflection profile of X-rays according to an angle of incidence of said X-rays on the interface;

means to determine an electronic density deficit at said interface from said reflection profile;

means to determine the adhesion energy from electronic density deficit adhesion models between rough surfaces.

2. Device according to claim 1, comprising means to detect X-rays and to store the coefficient of reflection of the detected X-rays.

3. Device according to claim 1, comprising means to determine a closure ratio defined as the ratio of the surfaces of said two layers actually in contact on nanometric scale to the total contact surface of said two layers from the electronic density deficit.

4. Device according to claim 3 comprising a calibration profile of bond energy in relation to the closure ratio, and means for comparing the determined closure ratio with the calibration profile.

5. Device according to claim 3, comprising a calibration profile of adhesion energy in relation to the electronic density deficit, and means for comparing said electronic density deficit with the calibration profile.

6. Device according to claim 1, said two layers being bonded together by molecular bonding.

7. A non-destructive method for measuring the adhesion energy at an interface between two layers, comprising:

measuring a reflection profile of X-rays according to an angle of incidence of said X-rays on the interface;

determining an electronic density deficit at said interface from said reflection profile;

determining the adhesion energy from electronic density deficit adhesion models between rough surfaces.

8. Method according to claim 7 comprising a low incidence X-ray reflection step on the interface.

9. Method according to claim 7 comprising comparison of the determined density deficit at the interface with a calibration profile.

10. A method according to claim 7, said two layers being bonded together by molecular bonding.

11. A non-destructive measurement device for measuring an adhesion energy at an interface between two layers, comprising:

means for measuring a reflection profile of X-rays according to an angle of incidence of said X-rays on the interface;

means to determine an electronic density deficit at said interface;

means to determine the adhesion energy from a calibration of said electronic density deficit.

12. Device according to claim 11, comprising means to detect X-rays and to store the coefficient of reflection of the detected X-rays.

13. Device according to claim 11, comprising means to determine a closure ratio defined as the ratio of the surfaces of said two layers actually in contact on nanometric scale to the total contact surface of said two layers from the electronic density deficit.

14. Device according to claim 13 comprising a calibration profile of adhesion energy in relation to the closure ratio, and means for comparing the determined closure ratio with the calibration profile.

15. Device according to claim 11, said two layers being bonded together by molecular bonding.

16. A non-destructive method for measuring the adhesion energy at an interface between two layers, comprising:

measuring a reflection profile of X-rays according to an angle of incidence of said X-rays on the interface;

determining an electronic density deficit at said interface from said reflection profile;

determining the adhesion energy from a calibration of said electronic density deficit.

17. A method according to claim 16 comprising a low incidence X-ray reflection step on the interface.

18. A method according to claim 16, said two layers being bonded together by molecular bonding.

* * * * *